United States Patent [19]
Kroll

[11] Patent Number: 5,257,634
[45] Date of Patent: Nov. 2, 1993

[54] LOW IMPEDENCE DEFIBRILLATION CATHETER ELECTRODE

[75] Inventor: Mark W. Kroll, Minnetonka, Minn.

[73] Assignee: Angeion Corporation, Plymouth, Minn.

[21] Appl. No.: 915,065

[22] Filed: Jul. 16, 1992

[51] Int. Cl.⁵ .............................................. A61N 1/05
[52] U.S. Cl. ..................................... 607/122; 607/128
[58] Field of Search ............... 128/783, 784, 785, 786, 128/419 P, 419 D, 799, 642

[56] References Cited

U.S. PATENT DOCUMENTS

| | | | |
|---|---|---|---|
| 3,760,812 | 9/1973 | Timm et al. | 128/784 |
| 4,321,931 | 3/1982 | Hou | 128/642 |
| 4,414,986 | 11/1983 | Dickhudt et al. | 128/785 |
| 4,716,888 | 1/1988 | Wesner | 128/785 |
| 4,989,617 | 2/1991 | Memberg et al. | 128/785 |

FOREIGN PATENT DOCUMENTS

WO92/13481 8/1992 PCT Int'l Appl. .

Primary Examiner—William E. Kamm
Assistant Examiner—George Manuel
Attorney, Agent, or Firm—Anthony G. Eggink

[57] ABSTRACT

A low impedence defibrillation catheter electrode having a high effective conductive length for implantation in the right ventricle of the heart. The catheter electrode conductive body has at least one flexible and resilient extension member extending angularly therefrom. The flexible and resilient conductive members provide an increased effective length to the catheter electrode and permit collapse into a small diameter configuration for insertion into an introducer structure for implantation through a venous approach.

23 Claims, 2 Drawing Sheets

LOW IMPEDENCE DEFIBRILLATION CATHETER ELECTRODE

BACKGROUND OF THE INVENTION

The present invention relates to implantable catheter electrodes and particularly to catheter electrodes that provide high effective length electrode structures utilizing electrode extension members which exhibit low electrical impedance.

The implantable cardioverter defibrillator (ICD) is a recognized and important therapy for patients with a propensity for ventricular fibrillation and hemodynamically-compromising tachycardias. Initially, ICD's required open-chest surgery to attach large electrodes, such as epicardial patch electrodes, to the epicardial surfaces of the heart. These procedures increased the mortality and expense associated with ICD implantation.

The present trend is towards the use of defibrillation catheters which, at a minimum, rest in the right ventricle of the heart. Unfortunately these catheter electrodes have higher electrical impedances than do the epicardial patches. This in turn demands a significantly increased voltage in order to provide a sufficient current for defibrillation. This current requirement results, therefore, in a significantly higher energy requirement for defibrillation.

The prior art defibrillation catheter electrodes have the maximum surface areas allowed by the anatomical constraints of the human heart. Nevertheless, their impedances are excessively high. There is, therefore, a need for a low impedance endocardial catheter electrode that will fit through the human veins and be able to reside in the right ventricle of the heart.

Mathematical analysis and laboratory testing has demonstrated that the surface area of a catheter electrode is not as important as is the electrode length for establishing a low impedance electrode. Thus, the object of the present invention is to provide a small diameter catheter electrode that has a large effective length.

SUMMARY OF THE INVENTION

A defibrillation catheter electrode for implantation into the right ventricle of the heart is provided by the present invention. The catheter electrode has a conductive body portion of a specified length and diameter and has at least one conductive extension member resiliently extending outward therefrom.

The conductive extension members provide an increased effective length of the electrode conductive body portion to provide a catheter electrode structure having a relatively low electrical impedance.

Various catheter electrode embodiments are provided by the present invention and which teach methods and structures for providing the conductive extension members which collapsably and resiliently extend from the respective electrode conductive bodies.

Further, methods are taught for introducing the catheter electrodes of this invention into the body for implantation.

These and other benefits of this invention will become clear from the following description by reference to the drawings.

DESCRIPTION OF THE PREFERRED EMBODIMENTS

Figure 1:
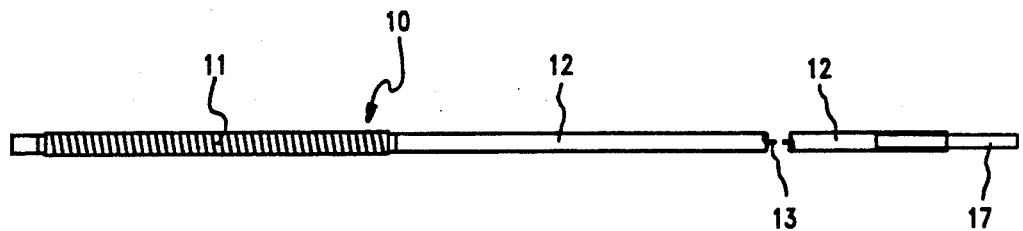
FIG. 1 is a lateral plan view of a typical prior art defibrillation catheter.
Figure 2:
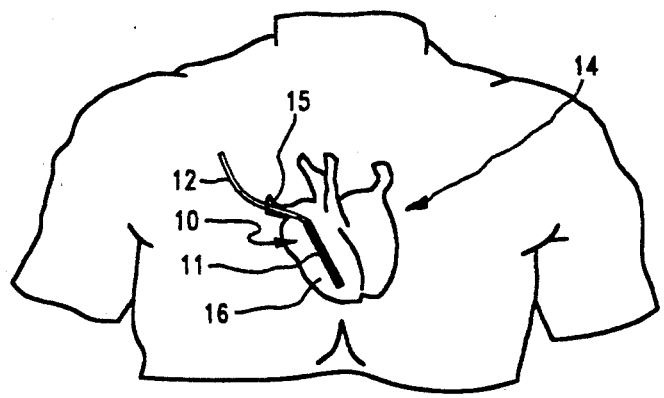
FIG. 2 is a frontal plan view showing the defibrillation catheter of the present invention placed in the right ventricle of the heart of a patient.

FIG. 1 shows a typical prior art defibrillation catheter 10 and FIG. 2 shows the prior art defibrillation catheter 10 placed through the superior vena cava 15 and in the right ventricle 16 of a patient's heart 14. The prior art catheter electrode 10 shown has an electrode conductive body portion 11 attached to lead 12 having a conductive lead member 13. At the end of lead 12, a connector end 17 is provided for connection to an implanted defibrillation system. The diameter of the electrode 10 conductive body portion 11 is approximately 4 mm and it typically has a length of approximately 6 cm. This is the maximum diameter that can be forced through a patient's veins and the 6 cm length is the maximum length that will reliably fit in the right ventricle 16. These dimensions provide an electrode surface area of approximately 750 mm$^2$. Thus, the prior art defibrillation catheter electrodes 10 have the maximum surface areas allowed by the anatomical constraints of the human heart. Nevertheless, as previously discussed, their impedances are excessively high.

Figure 3:
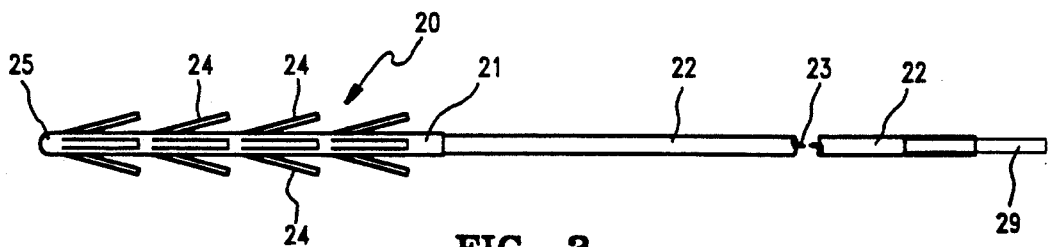
FIG. 3 is a lateral plan view showing the defibrillation catheter of the present invention.

FIG. 3 shows the defibrillation catheter electrode 20 of the present invention. The narrow catheter or small diameter electrode 20 has a conductive body 21 with plurality of protruding short conductor segments or extensions 24 along its length and around its circumference. The extension members 24 are in conductive contact with body 21 and are shown to be angularly disposed away from the electrode tip 25. As will be further described, the extension members 24 can be constructed and arranged on the electrode conductive body 21 in a variety of ways. The high effective length of the catheter electrode due to the extension members provides a low impedance electrode to the heart and blood pool when implanted in the right ventricle.

Figure 4:
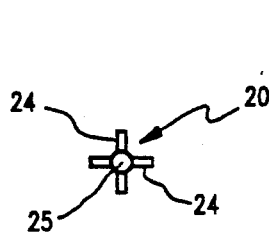
FIG. 4 is a frontal plan view showing the defibrillation catheter of FIG. 3.

FIG. 4 is an end view of the electrode 20, as shown in FIG. 3, and which shows four rows of four extension members 24 equidistantly positioned about the electrode conductive body 21. For optimal performance, the spacing between the tips of the extensions is approximately the length of the respective extension members 24. In other words, as viewed radially or cross-sectionally with respect to the length of the conductive body 21 in FIG. 3, the distance between the adjoining tips of extension members 24 is approximately the length of a single member 24. It is preferred in the teachings of this invention to add length to the extension members 24, rather than adding the number of members 24 in a specific row. Preferably, the extensions 24 are repeated about 3 to 5 times around a given circumference of the conductive catheter body 21. Importantly, the extensions 24 are able to be resiliently folded within an introducer sheath structure so that the catheter electrode can be introduced in a collapsed configuration through a venous approach without patient discomfort or risk. Upon arrival in the right ventricle 16, the introducer structure is pulled back, as known in the art, and the conducting extensions 24 spring back to extend outwardly in the right ventricle. The angular disposition of the extension members with respect to the conductive body of the electrode may be acute or obtuse, although a 90 degree angle is most effective for performance.

As will be further discussed, there are several methods or processes for attaching or providing the extensions 24 to the defibrillation electrode conductive body 21. For example, the extensions 24 can be wrapped into a ribbon and attached to the electrode body. Alternatively, the extensions 24 can be part of the same conductive braiding material that is used to braid the catheter body itself. These extensions are then snipped off after they leave the main braid. There is a broad range of useful numbers of extensions according to the teachings of this invention. For example, as few as 5 extensions will lower the impedance of the electrode while as many as 100 extensions are easily manufactured into the basic electrode. The important teaching of t is invention is to increase the effective conductive length of the catheter electrode and it is within the purview of this invention to have at least one to a plurality of conductive extension members whether or not aligned with respect to each other on the conductive electrode body.

Figure 5:
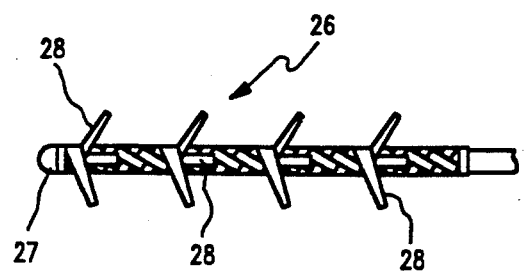
FIG. 5 is a perspective view showing an embodiment of the defibrillation catheter of the invention.

FIG. 5 is a perspective view which shows the defibrillation catheter electrode 26 having a braided conductive body 27 having a plurality of strands. The strands are constructed of conductive wire material which exhibit pliability and resilience. To provide the conductive extensions of this invention, specified strands can be cut to provide braid ends 28 which function as the conductive extension members.

Figure 6:
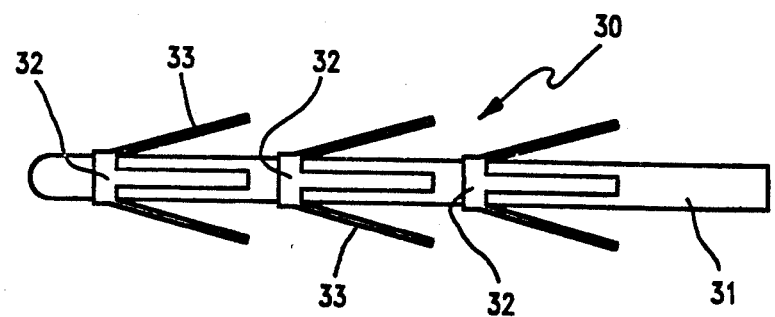
FIG. 6 is a lateral view showing another embodiment of the defibrillation catheter of the invention.

FIG. 6 is a lateral view showing the electrode conductive body portion 31 of the defibrillation catheter electrode 30 having a plurality of peripheral conductive bands 32 from which the electrode extension members 33 extend. The bands 32 are fastened to and in conductive contact with the electrode body 31 and the extension members 33 extend outwardly from the electrode body 31, as previously described.

Figure 7:
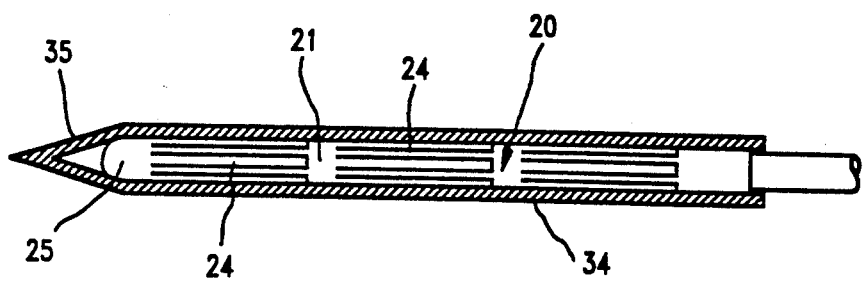
FIG. 7 is a lateral view showing the defibrillation catheter of the invention in a collapsed configuration for implantation.

FIG. 7 shows the defibrillation catheter electrode 20 in a collapsed configuration within an introducer structure 34 having forward end 35 for introduction into a vein of the body. As shown, the electrode extensions 24 are foldably and resiliently positioned whereby they are parallel to the electrode conductive body portion 21. After being positioned in the right ventricle of the heart, the catheter electrode 20 is removed from introducer 34 and the resilient extensions 24 spring back to their respective angularly disposed positions with respect to the conductive body portion 21.

Figure 8:
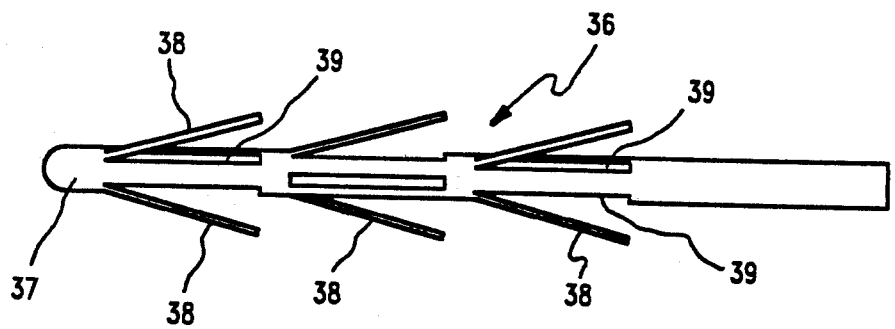
FIGS. 8 and 9 are perspective views showing embodiments of the defibrillation catheter of the invention.

FIG. 8 shows a defibrillation catheter electrode structure 36 wherein the electrode conductive body portion 37 has a plurality of pivotable extension members 38 which are cut from the body 37, thus, defining a plurality of cutout portions 39. This embodiment 36 permits the catheter structure to be collapsed into a thin or small diameter configuration for implantation purposes via the use of an introducer structure 34, as described with respect to FIG. 7.

Figure 9:
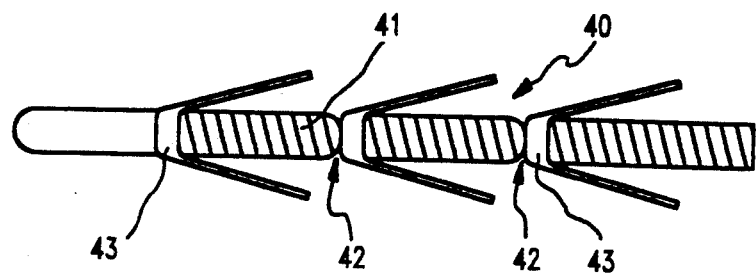

FIG. 9 shows a defibrillation catheter electrode 40 having a coiled conductive body portion 41 and having a number of spaced indented portions 42. The conductive extension members 43 are shown to be formed in a band configuration which are positioned in the indented portions 42.

In summary, the present invention provides an implantable defibrillation catheter electrode having at least one conductive extension member angularly disposed from the conductive body of the electrode. Because of the increased effective length of the catheter electrode of this invention the catheter conductive body may have a reduced diameter of approximately 1-2 mm. The length of the conductive body may be 6 cm. The extension members may be between 1-20 mm in length. Preferably, the total conductive length of the catheter electrodes of this invention is at least 10 cm, which total length is comprised of the conductive body length plus the length(s) of the extension members. The extension members can comprise any pattern on the conductive catheter body.

The extension members are preferably constructed of the same or similar material as that of the electrode conductive body portion. Typically, these materials are platinum, titanium, stainless steel, silver, alloys thereof, or like conductive materials. As discussed, it is important that the extension members be deformably and resiliently disposed on the conductive body so that they may be collapsed against the conductive body for implantation purposes. Subsequent to the removal of the introducer structure from the collapsed electrode structure the extension members spring back to their respective angularly disposed positions on the conductive body. The increased conductive length provided by the extension members reduce the electrical impedance of the defibrillation electrode of this invention.

As many changes are possible to the embodiments of this invention utilizing the teachings thereof, the descriptions above, and the accompanying drawings should be interpreted in the illustrative and not in the limited sense.

I claim:
1. A low impedance defibrillation catheter electrode having a high effective conductive length comprising:
   a) an electrode structure having an elongated conductive body having a predetermined first length and lead means extending therefrom for connection to a defibrillation system; and
   b) at least one resilient conductive member extending outwardly from said elongated conductive body and being unitary therewith, each of said at least one resilient conductive members(s) being a single elongated body having a predetermined second length, said second length being shorter than said first length, each of said at least one resilient conductive member(s) length comprising means for increasing the effective conductive length of said defibrillation electrode to thereby lower its impedance.

2. The defibrillation catheter electrode of claim 1, wherein the total length of said first and second lengths is at least 10 cm.

3. The defibrillation catheter electrode of claim 1, wherein said at least one conductive member of said elongated conductive body comprises a plurality of conductive members extending from said electrode conductive body in a predetermined arrangement.

4. The defibrillation catheter electrode of claim 3, wherein said elongated conductive body has a specified diameter and conductive surface area and said at least one resilient conductive member(s) extend(s) angularly from said conductive surface in a predetermined pattern of rows and columns.

5. The defibrillation catheter electrode of claim 1, wherein said elongated conductive body is comprised of a braided structure having a plurality of conductive strands, at least one said conductive strand of said plurality of conductive strands having a terminal end and wherein said at least one outwardly extending resilient conductive member is the terminal end of said at least one conductive strand.

6. The defibrillation catheter electrode of claim 1, wherein said elongated conductive body has at least one peripheral band conductively mounted thereabout and being unitary therewith and wherein said at least one resilient conductive member extends from said at least one peripheral band.

7. The defibrillation catheter electrode of claim 6, wherein said elongated conductive body has a plurality of peripheral bands being spaced apart a distance at least that of said conductive member length.

8. The defibrillation catheter electrode of claim 6, wherein said elongated conductive body has at least one peripheral groove thereabout and wherein said at least one peripheral band is mounted in said at least one peripheral groove.

9. A defibrillation catheter electrode comprising an elongated conductive body of a predetermined length and configuration and comprising means for pivotally connecting at least one outwardly extending conductive member and for reducing the electrode impedance, said at least one outwardly extending conductive member being unitary with said elongated conductive body.

10. The defibrillation catheter electrode of claim 9, wherein the total length of said elongated body and said conductive member(s) is at least 10 cm.

11. The defibrillation catheter electrode of claim 9, wherein each of said at least one conductive member has a diameter ranging between 1 and 2 mm and wherein each of said at least one conductive member has a length ranging between 1 and 20 mm.

12. The defibrillation catheter electrode of claim 11, further comprising at least one row of conductive members, extending from the periphery of said conductive body and a plurality of said conductive members spaced a predetermined distance from each other.

13. The defibrillation catheter electrode of claim 12, wherein said conductive members are spaced approximately said predetermined second length.

14. The defibrillation catheter electrode of claim 9, wherein said elongated conductive body is comprised of a braided structure having a plurality of conductive, flexible and resilient strands said plurality of resilient strands having terminal ends and wherein said at least one outwardly extending and pivotally connected conductive member is one said strand terminal end.

15. The defibrillation catheter electrode of claim 9, wherein between 3 to 5 conductive members extend from said elongated conductive body.

16. The defibrillation catheter electrode of claim 15, wherein said conductive members are not aligned along the length of said conductive body.

17. The defibrillation catheter electrode of claim 16, wherein said conductive members are spaced in a row about the periphery of said conductive body.

18. The defibrillation catheter electrode of claim 9, further comprising an introducer sheath structure wherein said catheter electrode is, surrounded by said sheath in a collapsed configuration having said outwardly extending member(s) pivoted against said conductive body.

19. The defibrillation catheter electrode of claim 9, wherein a conductive peripheral band is in conductive contact about said conductive body and wherein said at least one outwardly extending member is connected to said peripheral conductive band.

20. A process of implanting a low electrical impedance defibrillation catheter electrode through the veins and into the right ventricle of the heart of a patient comprising:
   a) providing a defibrillation catheter electrode having an elongated conductive body and at least one outwardly extending pivotally connected conductive member and being unitary with said conductive body,
   b) providing an introducer sheath structure having an opening,
   c) inserting said defibrillation catheter electrode into said sheath structure and thereby collapsing said catheter structure by folding said conductive member against said conductive body,
   d) manipulating said introducer sheath structure into the right ventricle of the heart, and
   e) removing said introducer sheath structure from said collapsed catheter structure, thereby permitting said conductive members to pivot from said conductive body into an angular configuration.

21. In a defibrillation catheter electrode having an electrode body having a lead assembly electrically connecting said electrode body and a defibrillator device, said electrode body comprising a plurality of conductive body members extending from said electrode body, each said conductive body member having a predetermined length and opposing conductive surfaces and being unitary with said electrode body and comprising resilient means for exposing said conductive surfaces and conductive means for lowering the impedance of the defibrillation catheter electrode.

22. The defibrillation catheter electrode of claim 21, wherein each said conductive body member is of a planar configuration.

23. The defibrillation catheter electrode of claim 22, wherein each said planar body member is arranged in a plurality of rows along said electrode body.

* * * * *